United States Patent [19]

Corey

[11] 4,086,266
[45] Apr. 25, 1978

[54] METHOD OF BACTERIALLY PURIFYING METHYL CYANOACRYLATE

[75] Inventor: Harold Corey, Teaneck, N.J.

[73] Assignee: Population Research Incorporated, Clearwater, Fla.

[21] Appl. No.: 784,956

[22] Filed: Apr. 6, 1977

[51] Int. Cl.² ............................................. C07C 121/30
[52] U.S. Cl. .................................................. 260/465.4
[58] Field of Search ............................ 260/465.4; 21/2

[56] References Cited

U.S. PATENT DOCUMENTS

| | | | |
|---|---|---|---|
| 2,763,677 | 9/1956 | Jeremias | 260/465.4 |
| 3,250,002 | 5/1966 | Collito | 260/465.4 X |
| 3,360,124 | 12/1967 | Stonehill | 260/465.4 UX |
| 3,527,841 | 9/1970 | Wicker, Jr. et al. | 260/823 |
| 3,564,078 | 2/1971 | Wicker, Jr. et al. | 260/465.4 X |
| 3,699,076 | 10/1972 | Thomsen et al. | 128/155 X |
| 3,759,264 | 9/1973 | Coover, Jr. et al. | 128/334 R |
| 3,822,702 | 7/1974 | Bolduc et al. | 128/235 |
| 3,948,259 | 4/1976 | Bolduc et al. | 128/235 |

FOREIGN PATENT DOCUMENTS 1,159,548  7/1969  United Kingdom .............. 260/465.4

*Primary Examiner*—Joseph Paul Brust
*Attorney, Agent, or Firm*—Schroeder, Siegfried, Ryan, Vidas & Steffey

[57] ABSTRACT

A process is described whereby methyl cyanoacrylate (MCA) may be bacterially made sterile without the degradation of the product by partial or total polymerization and without the introduction of or creation of materials which are adverse to the use of the MCA in vivo in the human body. The process utilizes a filtration technique including a polytetrafluoroethylene (Teflon) filter element.

9 Claims, No Drawings

METHOD OF BACTERIALLY PURIFYING METHYL CYANOACRYLATE

The present invention is directed to a process for the sterilization of monomeric (or low molecular weight polymer) of methyl cyanoacrylate without the necessity of using relatively large amounts of polymerization inhibitors as has commonly been the practice in the prior art. Methyl cyanoacrylate (MCA) is a well-known chemical product that has found wide use in the medical field for a variety of purposes as a tissue adhesive. More recently, MCA has found application in the field of permanent sterilization of human females. Sterilization in the female is accomplished by introduction of small quantities of MCA into the fallopian tubes whereby its contact with body moisture the MCA polymerizes and blocks the fallopian tube. With passage of time, fibrous tissue growth replaces the MCA and permanent sterilization results. This use and procedure is described in the U.S. Pat. Nos. 3,822,702 and 3,948,259.

However, the very properties which make MCA desirable for use as an adhesive for medical purposes, such as the binding of wound edges together, also make it a difficult material to sterilize. MCA polymerizes under a variety of conditions including exposure to even trace amounts of moisture, heat, high energy radiation, etc. It is also a problem to store for any period of time due to its tendency to autocatalyze itself and become a solid cured polymer in storage. It is known that one can add quantities of inhibitor substances (generally in a range of 100–600 ppm) to the MCA to greatly reduce any tendency to autocatalyze itself during storage. However, in order to prevent curing during the prior art techniques for sterilization (which generally use elevated temperatures), relatively large amounts of such inhibitors must be utilized.

In the prior art techniques for sterilization of MCA, the substantially monomeric material is heated to effect sterilization. Prior patents teaching such sterilization by the use of heat include U.S. Pat. Nos. 3,564,078; 3,699,076; 3,527,841 and British Pat. No. 1,159,548. In U.S. Pat. No. 3,360,124, there is described a process for sterilization of MCA which involves sealing the MCA in tin containers and heating to bring about sterilization. In order to prevent the polymerization during the sterilization, it has been proposed to use sulfur dioxide, nitrogen oxide, phosphoric acid, etc. Free radical scavengers may also be employed as stabilizers such as hydroquinone and the like. These are dealt with in some detail in the patents cited immediately above. While such inhibitors function to prevent or minimize polymerization that is undesired, they do have an adverse effect on the desired ultimate use of the sterilized material by their presence in the quantities necessary to provide their presence in the quantities necessary to provide inhibition.

I have found that MCA monomer may be effectively sterilized without the need for the use of inhibitors at all or by use of small quantities of inhibitors at levels well below those of prior art. A low level of inhibitor is desirable in the finished product to prevent autocatalyzation during storage. This quantity is markedly less than is necessary as an antipolymerizer for prior art heat sterilization which is the most commonly used sterilization procedure of the prior art.

It should be understood that the sterilization procedures of the present invention are applicable to the various forms of cyanoacrylate materials that have been found useful in surgical procedures. That is, the invention is not limited to the bacterial sterilization of monomeric methyl cyanoacrylate but can be utilized in the sterilization of all of the monomeric esters of aliphatic cyanoacrylates described in U.S. Pat. Nos. 2,763,677 or 3,759,264. For purposes of the description of the invention, MCA is utilized as an example only. When the term monomeric polymer is used herein, it is intended to include the monomer and mixtures therewith of dimers or trimers where these mixtures are substantially monomers and are liquid substances at room temperatures.

In accordance with the present invention, it has been found that the cyanoacrylate monomers may be rendered bacterially and, of course, fungicidally pure through use of filtering techniques utilizing special filter elements that are pretreated in accordance with the invention. It is known to filter liquids using fine filters to remove bacteria. However, when such techniques have been tried with cyanoacrylates, the conditions of filtration have brought about polymerization of the cyanoacrylate and resulted in clogging of the filter. Even when relatively large amounts of inhibitor are used, the results of attempted filtration have been less than satisfactory and the resulting product (when filtration has achieved any degree of success) has included undesired quantities of the inhibitors.

In the present invention, I have overcome the problems of removing bacteria by use of a polytetrafluoroethylene-type filter that is first baked to remove to the extent possible any water or other volatile polymerizing agents from the surface of the filter prior to passing the cyanoacrylate therethrough. It is my belief that a principal reason that fine glass frit filters cannot be successfully used for filtering cyanoacrylate is that the absorbed moisture on the glass surface is virtually impossible to remove as completely as is required. This moisture layer on the filter triggers the polymerization of the cyanoacrylate and the result is a blocking of the filter.

An example of the procedure of my invention follows. The procedure will be described with regard to bacterial filtering of methyl cyanoacrylate (MCA) although it will be understood that other similar aliphatic cyanoacrylates respond to the same procedure. A substantially monomeric methyl cyanoacrylate is prepared using the procedures described in U.S. Pat. No. 2,763,677. It is purified by vacuum distillation to yield better than 99% pure monomeric MCA. The monomer so produced is then directly filtered through a Teflon filter in accordance with the invention. As catalytic sites have been removed from the filter, as will be described below, there is no need for inclusion of polymerization inhibitors at the filtration stage. If the purified and sterile MCA is to be stored for any significant length of time, the addition of a small quantity of polymerization inhibiting agent such as a Lewis acid which is one of hydroxy propyl sulfonic acid, methyl sulfonic acid, phosphoric and isethionic acid is desirable. I have found that isethionic acid and phosphoric acid are preferred for the purpose. Alternatively, one may use suldioxide with a free radical inhibitor such as hydroquinone or an antioxidant such as butylated hydroxy toluene. Quantities generally below 100 ppm and preferably below 50 ppm are recommended. The bacterial filtration may be made without the addition of any inhibitor, but as small quantities are desirable for prolonged shelf life after bacterial purification, the inclusion during filtration of such small quantities gives an added degree of safety against undesired polymerization subsequent to the filtration step. Such undesired polymerization during storage can occur as a result of contact with catalysts in the storage container, such as, absorbed moisture, radiant energy, etc. As noted above, one may also include an antioxidant to further stabilize the MCA against polymerization during storage. A suitable antioxidant is butylated hydroxytoluene (BHT). This latter material is not a required addition. Various other antioxidants as taught in the art may also be used.

The preferred filter element is a 0.2 micrometer pore Teflon (polytetrafluoroethylene) filter such as is available from the Millipore Corporation under the trade name "FLUOROPORE." Filter elements for use in the invention are made of a polyethylene network which has had bonded thereto a polytetrafluoroethylene layer to provide a porous structure with a maximum pore diameter of about 0.2 micrometer. The filter element and related and connective equipment is sterilized by steam autoclaving at about 121° C. Prior to use, the filter element and other connected apparatus is vacuum baked at a temperature up to about 100° C to desorb water or other volatile catalytic materials from the surface of the filter and connected system. Although it is not necessary one may, as an additional precaution, flood the apparatus with dry ethylene oxide and again vacuum bake. The filter at this stage is both bacterially sterile and has had any residual adsorbed water vapor removed therefrom.

The monomeric MCA is then filtered through the previously sterilized and vacuum baked Teflon filter element with the aid of pressure of 18-20 psi or even higher to collect the bacteria-free monomeric MCA. It is advantageous to use a double Teflon filter with the source side filter element having a pore size of 5-10 μm to remove foreign particulate matter prior to the MCA coming into contact with the 0.2 μm filter element. A laminate or sandwich arrangement of filter element is the result. The purified MCA is then transferred to the desired storage vessels for the later use.

What I claim is:

1. The method of providing a bacterially sterile monomer of an aliphatic cyanoacrylate comprising:
    (a) preparing a substantially monomeric aliphatic cyanoacrylate that is greater than 99% pure monomer;
    (b) providing a sterilized Teflon filter element having a pore size of about 0.20 micrometer;
    (c) treating said Teflon filter element by vacuum heating to a temperature of about 100° C to desorb water and substantially all other volatile polymerization catalyst materials from the surface of the filter element; and,
    (d) filtering said monomeric aliphatic cyanoacrylate through said Teflon filter element to remove all bacteria therefrom.

2. The method in accordance with claim 1 wherein the filter element is flushed with ethylene oxide gas subsequent to vacuum heating and revacuumed to remove the ethylene oxide.

3. The method in accordance with claim 1 wherein a small quantity, below about 100 ppm, of a Lewis acid polymerization inhibitor is added to said aliphatic cyanoacrylate prior to passage through said filter element.

4. The method in accordance with claim 3 wherein said polymerization inhibitor is selected from the group consisting of sulfur dioxide, isethionic acid and phosphoric acid.

5. The method in accordance with claim 1 wherein a small quantity, below about 100 ppm, of the polymerization inhibitor selected from the group hydroquinone and butylated hydroxy toluene is added to the aliphatic cyanoacrylate prior to passing through said filter element.

6. The method in accordance with claim 1 wherein said aliphatic cyanoacrylate monomer is methyl cyanoacrylate.

7. The method in accordance with claim 6 wherein a small quantity, below about 100 ppm, of a Lewis acid is added to said methyl cyanoacrylate prior to filtering it through said filter element.

8. The method in accordance with claim 6 wherein the Lewis acid is isethionic acid.

9. The method in accordance with claim 1 in which the filtering step is accomplished with the aid of pressure.

* * * * *